United States Patent [19]

Berg

[11] Patent Number: 5,776,321
[45] Date of Patent: Jul. 7, 1998

[54] SEPARATION OF T-AMYL ALCOHOL FROM 1-PROPANOL BY AZEOTROPIC DISTILLATION

[76] Inventor: Lloyd Berg, 1314 S. 3rd Ave., Bozeman, Mont. 59715

[21] Appl. No.: 865,896

[22] Filed: May 30, 1997

[51] Int. Cl.⁶ ............................. B01D 3/36; C07C 29/84
[52] U.S. Cl. ............................. 203/57; 203/58; 203/60; 203/62; 203/68; 203/69; 203/63; 203/70; 568/913
[58] Field of Search ............................. 203/57, 58, 60, 203/62, 68, 69, 70, 63; 568/913

[56] References Cited

U.S. PATENT DOCUMENTS

| | | | |
|---|---|---|---|
| 2,559,519 | 7/1951 | Smith, Jr. et al. | 203/64 |
| 2,559,520 | 7/1951 | Smith, Jr. et al. | 203/64 |
| 2,591,712 | 4/1952 | Morrell et al. | 203/52 |
| 2,706,707 | 4/1955 | Morrell et al. | 203/53 |
| 4,416,734 | 11/1983 | Jacobs | 203/63 |
| 4,693,787 | 9/1987 | Berg et al. | 203/64 |
| 4,693,788 | 9/1987 | Berg et al. | 203/57 |
| 4,756,803 | 7/1988 | Berg | 568/913 |
| 4,935,103 | 6/1990 | Berg | 203/65 |
| 5,332,478 | 7/1994 | Berg | 203/62 |
| 5,338,410 | 8/1994 | Berg | 203/57 |
| 5,360,520 | 11/1994 | Berg | 203/60 |

Primary Examiner—Virginia Manoharan

[57] ABSTRACT

1-Propanol cannot be separated from t-amyl alcohol by distillation or rectification because of the closeness of their boiling points. 1-Propanol is readily separated from t-amyl alcohol by azeotropic distillation. Effective agents are heptane, ethyl acetate and tetrahydrofuran.

1 Claim, No Drawings

SEPARATION OF T-AMYL ALCOHOL FROM 1-PROPANOL BY AZEOTROPIC DISTILLATION

FIELD OF THE INVENTION

This invention relates to a method of separating t-amyl alcohol from 1-propanol using certain organic liquids as the agent in azeotropic distillation.

DESCRIPTION OF PRIOR ART

Azeotropic distillation is the method of separating close boiling compounds or azeotropes from each other by carrying out the distillation in a multiplate rectification column in the presence of an added liquid, said liquid forming an azeotrope with one or more of the compounds to be separated. Its presence on each plate of the rectification column alters the relative volatility in a direction to make the separation on each plate greater and thus require either fewer plates to effect the same separation or make possible a greater degree of separation with the same number of plates. The azeotrope forming agent is introduced with the feed to a continuous column. The azeotrope forming agent and the more volatile component are taken off as overhead product and the less volatile component comes off as bottoms product. The usual methods of separating the azeotrope former from the more volatile component are cooling and phase separation or solvent extraction.

The usual method of evaluating the effectiveness of azeotropic distillation agents is the change in relative volatility of the compounds to be separated. Table 1 shows the degree of separation or purity obtainable by theoretical plates at several relative volatilities. Table 1 shows that a relative volatility of at least 1.2 is required to get an effective separation by rectification.

TABLE 1

Effect of Relative Volatility on Theoretical stage Requirements.

| Separation Purity, | Relative Volatility | | | | | | | |
|---|---|---|---|---|---|---|---|---|
| Both Products (Mole Fraction) | 1.02 | 1.1 | 1.2 | 1.3 | 1.4 | 1.5 | 2.0 | 3.0 |
| | Theoretical Stages at Total Reflux | | | | | | | |
| 0.999 | 697 | 144 | 75 | 52 | 40 | 33 | 19 | 12 |
| 0.995 | 534 | 110 | 57 | 39 | 30 | 25 | 14 | 9 |
| 0.990 | 463 | 95 | 49 | 34 | 26 | 22 | 12 | 7 |
| 0.98 | 392 | 81 | 42 | 29 | 22 | 18 | 10 | 6 |
| 0.95 | 296 | 61 | 31 | 21 | 16 | 14 | 8 | 4 |
| 0.90 | 221 | 45 | 23 | 16 | 12 | 10 | 5 | 3 | t-Amyl alcohol and 1-propanol boil five degrees apart and have a relative volatility of 1.18 which makes it impossible to separate them by conventional distillation or rectification. Table 2 shows that with an agent giving a relative volatility of 1.65, only 26 actual plates are required to get 99% purity.

TABLE 2

Theoretical and Actual Plates Required vs. Relative volatilty for 1-Amyl Alcohol from 1-Propanol Separation

| Relative Volatility | Theoretical Plates Required At Total Reflux, 99% Purity | Actual Plates Required, 75% Eff. |
|---|---|---|
| 1.3 | 34 | 46 |
| 1.4 | 20 | 35 |
| 1.65 | 19 | 26 |

OBJECTIVE OF THE INVENTION

The object of this invention is to provide a process or method of azeotropic distillation that will enhance the relative volatility of t-amyl alcohol from 1-propanol in their separation in a rectification column. It is a further object of this invention to identify effective azeotropic distillation agents that are stable and can be recycled.

SUMMMARY OF THE INVENTION

The objects of this invention are provided by a process for the separation of t-amyl alcohol from 1-propanol which entails the use of certain organic compounds when employed as the agent in azeotropic distillation.

TABLE 3

Effective Azeotropic Distillation Agents For Separating t-Amyl Alcohol From 1-Propanol

| Compounds | Relative Volatility |
|---|---|
| None | 1.18 |
| Methyl acetate | 1.6 |
| Ethyl acetate | 1.7 |
| Isopropyl acetate | 1.55 |
| Butyl formate | 1.45 |
| Di-tert. butyl formate | 1.45 |
| Methyl pivalate | 1.6 |
| Methyl propionate | 1.45 |
| Ethyl propionate | 1.6 |
| Acetone | 1.45 |
| 2-Butanone | 1.45 |
| Cyclopentane | 1.55 |
| Benzene | 1.7 |
| Cyclohexane | 1.7 |
| Cyclohexene | 1.65 |
| 1-Octene | 1.65 |
| Octane | 1.75 |
| Isooctane | 1.7 |
| 2,2,4-Trimethylpentane | 1.7 |
| Hexane | 1.6 |
| t-Butyl methyl ether | 1.55 |
| Petroleum ether | 1.55 |
| Dimethoxymethane | 1.6 |
| Nitroethane | 1.45 |
| Heptane | 1.7 |
| Toluene | 1.6 |
| Methyl cyclohexane | 1.65 |
| Tetrahydrofuran | 1.55 |
| Ethyl formate | 1.65 |

DETAILED DESCRIPTION OF THE INVENTION

I have discovered that certain organic compounds will effectively increase the relative volatility between t-amyl alcohol and 1-propanol during rectification when employed as the agent azeotropic distillation. They are methyl acetate, ethyl acetate, isopropyl acetate, butyl formate, di-tert. butyl formate, methyl pivalate, methyl propionate, ethyl propionate, acetone, 2-butanone, cyclopentane, benzene, cyclohexane, cyclohexene, 1-octene, octane, isooctane, hexane, 2,2,4-trimethylpentane, t-butyl methyl ether, petroleum ether, dimethoxymethane, nitroethane, heptane, toluene, methyl cyclohexane, tetrahydrofuran and ethyl formate.

THE USEFULNESS OF THE INVENTION

The usefulness of this invention can be demonstrated by referring to the data presented in Tables 1, 2 and 3. All of the successful agents show that t-amyl alcohol can be separated from 1-propanol by means of azeotropic distillation in a rectification column and that the ease of separation as measured by relative volatility is considerable.

WORKING EXAMPLE

1. Fifty grams of 1-propanol-t-amyl alcohol mixture and fifty grams of heptane were charged to a vapor-liquid equilibrium still and refluxed for two hours. The vapor composition was 78.9% 1-propanol and 21.1% t-amyl alcohol; the liquid composition was 68.3%-propanol and 31.7% t-amyl alcohol. This is a relative volatility of 1-propanol to t-amyl alcohol of 1.7.

I claim:

1. A method for recovering 1-propanol from a mixture of 1-propanol and t-amyl alcohol which consists essentially of distilling a mixture consisting of 1-propanol and t-amyl alcohol in the presence of an azeotrope forming agent, recovering the 1-propanol and the azeotrope forming agent as overhead product and obtaining the t-amyl alcohol as bottoms product, wherein said azeotrope forming agent consists essentially of one material selected from the group consisting of methyl acetate, ethyl acetate, isopropyl acetate, butyl formate, methyl pivalate, di-tert. butyl formate, methyl propionate, ethyl propionate, acetone, 2-butanone, cyclopentane, benzene, cyclohexane, cyclohexene, 1-octene, octane, isooctane, 2,2,4-trimethylpentane, hexane, t-butyl methyl ether, petroleum ether, dimethoxymethane, nitroethane, heptane, toluene, methylcyclohexane, tetrahydrofuran and ethyl formate.

* * * * *